United States Patent [19]

Manske

[11] 4,141,379
[45] Feb. 27, 1979

[54] CHECK VALVE

[75] Inventor: Reinhold R. Manske, Hayward, Calif.

[73] Assignee: Cutter Laboratories, Inc., Berkeley, Calif.

[21] Appl. No.: 796,923

[22] Filed: May 16, 1977

[51] Int. Cl.$^2$ ............................................. F16K 15/14
[52] U.S. Cl. ............................. 137/496; 128/214 R; 137/517; 137/550; 137/859; 210/117
[58] Field of Search ...................... 128/214 R, 274; 137/496, 550, 859, 854, 517; 210/117, 430

[56] References Cited

U.S. PATENT DOCUMENTS

| | | | |
|---|---|---|---|
| 1,564,061 | 12/1925 | Hale | 137/550 |
| 1,897,572 | 2/1933 | Cornell | 210/117 |
| 2,462,189 | 2/1949 | Hess | 137/496 |
| 2,497,906 | 2/1950 | Peters et al. | 137/496 |
| 2,674,262 | 4/1954 | Bradshaw | 137/517 |
| 3,179,122 | 4/1965 | Wasdell | 137/854 X |

FOREIGN PATENT DOCUMENTS

| | | | |
|---|---|---|---|
| 897679 | 7/1949 | Fed. Rep. of Germany | 137/859 |
| 205022 | 5/1939 | Switzerland | 137/859 |
| 1222052 | 2/1971 | United Kingdom | 137/859 |

OTHER PUBLICATIONS

Pneumatic Diode; IBM Technical Disclosure Bulletin, vol. 5, No. 11, Apr. 1963.

Primary Examiner—Robert G. Nilson
Attorney, Agent, or Firm—Bertram Bradley; Robert E. Allen; James A. Giblin

[57] ABSTRACT

An improved check valve is disclosed for use in a system for sequentially delivering primary and secondary solutions through a common conduit. The check valve comprises a hollow housing with an inlet and an outlet connected to an enlarged intermediate portion. Sealed at its periphery in the enlarged portion is a flexible diaphragm characterized by having foraminous means in at least its outer portion and imperforate means in its central portion. The imperforate means is spaced from a valve seat surrounding the passage at the inner end of the inlet so that when the primary solution flows from the inlet to the outlet, it will pass freely around the imperforate means and through the foraminous means. When an increase in pressure, even though slight, is exerted against the diaphragm caused by flow of the secondary solution in the direction of the outlet to the inlet, the diaphragm moves towards the inlet causing the imperforate means to seal against the valve seat and stop the flow of the primary solution.

6 Claims, 9 Drawing Figures

CHECK VALVE

BACKGROUND OF THE INVENTION

This invention relates to disc valves and more particularly to improved disc valves which effect stoppage of liquid flow in response to slight back pressures against the valve.

There are many occasions where is it desirable to have two or more sources of liquid flow sequentially through a common feed line without the need for an operator to be present to manipulate controls so that liquid from secondary sources will flow through the common line when liquid from a primary source has been depleted. This is desirable particularly in the medical field when parenteral solutions are being administered to patients. On occasions, while a primary solution is being administered it is necessary to give an additive solution without its being diluted by the primary solution. If the volume of the additive solution is small, it can be introduced rapidly under pressure by hypodermic syringe through a medicinal entry or injection bulb included in the set for that purpose. An administration set such as that disclosed in U.S. Pat. No. 2,999,499 shows how this can be accomplished. When an additive solution is injected, check valve 22 serving as the medicinal entry, the considerable pressure exerted causes the disc in disc valve 9 to close the inlet from the primary solution so that the additive enters the patient's vein undiluted. However, when larger volumes of an additive or a secondary solution are to be administered, particularly over a prolonged period of time, such an arrangement is not workable since the secondary solution is introduced under considerably less pressure, a pressure generally insufficient to close off the disc valve in the primary line.

In U.S. Pat. No. 3,886,937 there is disclosed an administration set which is adapted for the introduction of a secondary solution under low pressures over prolonged periods without the need for manipulation by an attendent. This procedure is accomplished by means of a duck bill check valve in the primary line which is normally closed but which will open to the flow of liquid from a primary source by gravity and close if a secondary solution is introduced in the line below the valve which has a head pressure greater than the head pressure of the primary source by at least one inch of water. Although this type of check valve has considerable merit for such use in administration of additive solutions, it has certain drawbacks. The chief problem is that in the manufacture of the resilient duck bill member, the lips do not always come together in a closed manner and often leave an opening between them which is difficult to detect. This results in an incompetant valve which may not close with a very small back pressure exerted by the secondary solution. Particulates can also become lodged between the lips of the valve and prevent closure.

SUMMARY OF THE INVENTION

These problems have been overcome by a very special disc valve which assures that closure of a conduit from the inlet side of the valve leading to a primary solution container will be effected when even a slight increase of pressure is exerted on the outlet side of the valve by a secondary solution. The disc valve of this invention comprises a flexible diaphragm whose peripheral edges are sealed in an enlarged intermediate portion of an elongated hollow housing. The diaphragm has foraminous means in at least its outer portions and imperforate means at its central portion. The diaphragm normally is spaced a small distance from a valve seat which surrounds an inlet passage leading into the enlarged portion of the housing. In one modification of the disc valve, support means are located in the outlet side of the enlarged portion of the housing to help support the central portion of the diaphragm when liquid flows from the inlet to the outlet. The flow of liquid from a secondary container which is connected to the outlet, this secondary liquid having a head pressure of at least about one inch of water greater than the head pressure of the primary liquid, will cause the diaphragm to flex upwardly so that the imperforate means makes sealing contact with the valve seat and stops the liquid flowing from the primary container. When the head pressure of the primary solution exceeds that from the secondary solution, flow of the primary solution will resume.

The invention will be better understood and additional advantages will become apparent from the description and claims which follow.

DESCRIPTION OF PREFERRED EMBODIMENTS

Figure 1:
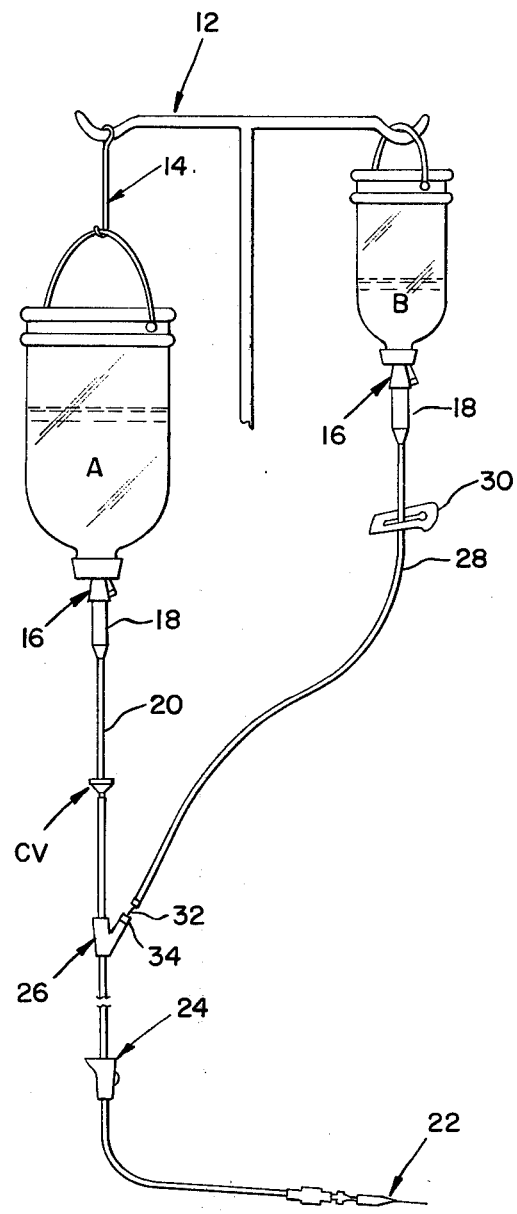
FIG. 1 is a front elevational view of an administration set connected to a primary solution container and to a secondary solution container, the secondary container being supported so that the secondary solution has a head pressure greater than the head pressure of the primary solution.

FIG. 1 illustrates an administration set employing the disc valve or check valve CV of this invention for dispensing a primary solution A and a secondary solution B in a sequential manner to a patient. Initially a container of primary solution A is suspended from hanger 12 by a wire extension 14 and entry is made through the closure of the container with an air inletting spike 16 to which is usually joined a drip chamber 18. Connecting conduit 20 has a needle 22 at the far end and a flow control device 24 such as a roller clamp situated at a position below a Y-adapter 26. Check valve CV is placed in conduit 20 between the Y-adapter 26 and the entry spike 16. In the usual procedure, by allowing solution A to flow through conduit 20, air is thereby purged from the set. Clamp 24 is closed until venipuncture is made and then it is adjusted for the desired rate of infusion of primary solution A as indicated by counting drops in drip chamber 18.

Should a secondary or additive solution B be required for infusion, a container of solution B is suspended from hanger 12 and a second conduit 28 is attached by means of entry spike 16. When conduit 28 is cleared of air by solution B, conduit 28 is closed with clamp 30 and conduit 28 is connected to conduit 20 by inserting needle 32 through a resealable cap 34 secured on one leg of the Y-adapter 26. When clamp 30 is released, the level of solution B in its container being higher than the level of solution A will cause solution B to flow upwardly in conduit 20 and close check valve CV. Flow of solution A ceases and solution B then infuses into the patient at a desired rate as controlled by clamp 24. When the head pressure for solution B becomes less than the head pressure for solution A, as when the level of solution B reaches a point below the level of solution A, then flow of solution A resumes. Check valve CV is responsive to very slight differences in head pressure between solution A and solution B. The head pressure of solution B needs to be only about one inch of water greater than that of solution A in order for check valve CV to close. In the open position, check valve CV is still capable of passing several liters an hour.

Figure 2:
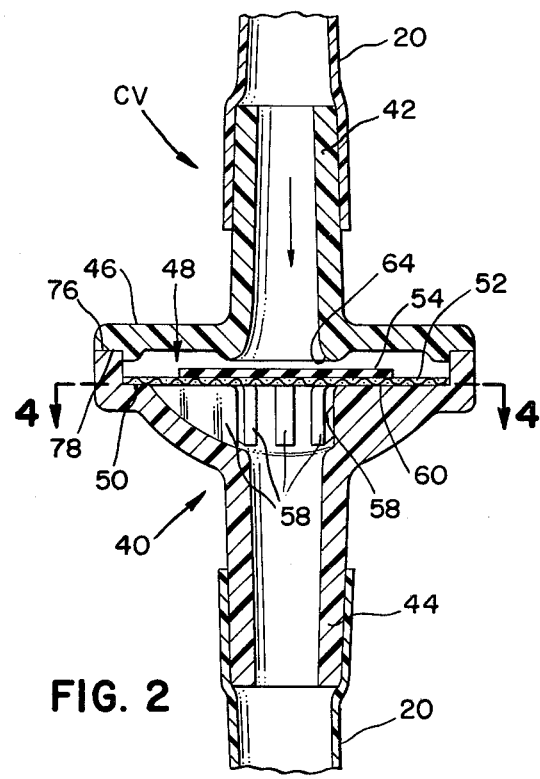
FIG. 2 is an elevational view in cross-section of an embodiment of the disc valve of the present invention taken along line 2—2 of FIG. 4, the valve of this view being in an open position.
Figure 3:
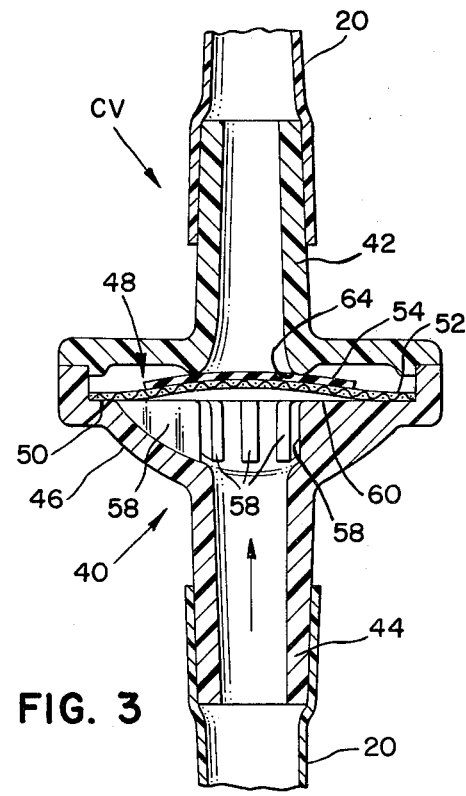
FIG. 3 is an elevational view in cross-section of the valve of FIG. 2 but with the valve shown in a closed position.
Figure 4:
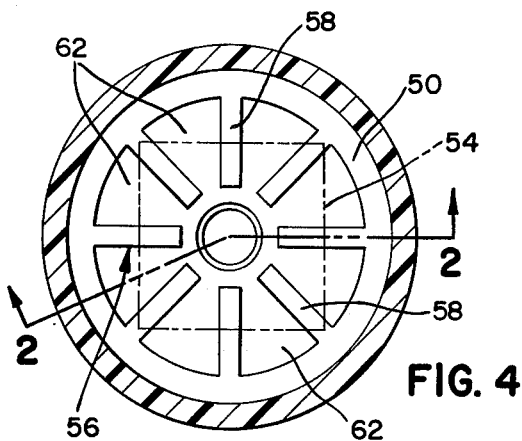
FIG. 4 is a sectional view taken along line 4—4 of FIG. 2 and showing imperforate means in phantom lying on top of support means.

To understand how check valve or disc valve CV functions, attention is directed to the embodiment as shown in FIGS. 2-4. The valve comprises an elongated housing 40 having an inlet 42 and an outlet 44 and an enlarged intermediate portion 46 whose cross-sectional area is somewhat greater than that of the inlet or outlet. A flexible diaphragm 48 spans the enlarged portion transversely to the inlet and outlet and is sealingly secured at its periphery to a shoulder 50 (best seen in FIGS. 4 and 5) in the housing 40.

Flexible diaphragm 48 can be made in a variety of ways as long as it conforms to the requirement that it has imperforate means in a central portion for engaging and sealing a valve seat and that it also has a plurality of apertures in the portion between the imperforate means and the periphery which is sealed to shoulder 50. In the embodiment shown in FIGS. 2-4, flexible diaphragm 48 consists of a screen 52 and a thin resilient disc 54 which either rests loosely on screen 52 or it can be secured to the screen as with a thin layer of adhesive. Screen 52 can be any flexible material such as metal or polymeric material which is physiologically acceptable and is non-swelling. One such material which is preferred is polyethylene terephthalate. Screen 52 can be a thin sheet with a large number of small holes or it can be woven, preferably to provide pores of about 5 to 75 microns in size.

Disc 54 is made of any non-sticking, resilient material such as natural or synthetic rubber or plastic. It can be a variety of shapes, round, square, irregular, as long as it covers enough area to seal a valve seat and yet allows liquids to flow readily around its edges and through screen 52. In this embodiment, disc 54 is preferably square and about the size shown in phantom in FIG. 4 in relation to the cavity inside the enlarged portion 46 of housing 40.

Housing 40 preferably has screen support means 56 which in the embodiment shown in FIGS. 2-4 consists of eight ribs 58 extending from the inner wall adjacent the outlet 44 of the enlarged portion 46 of housing 40. The ribs 58 each has a top surface 60 which provide a flat platform on which the screen 52 rests. When a primary solution A flows into check valve CV, it flows around disc 54 and through open areas 62 of screen 52 between ribs 58 and down through outlet 44. When a secondary solution B flows upwardly through outlet 44, even though the pressure at the outlet side may be as little as about one inch of water greater than the pressure at the inlet side, screen 52 will flex upwardly as in FIG. 3 so as to press disc 54 against valve seat 64 and stop the flow of solution A.

The effectiveness of check valve CV at these low pressure differentials is dependent on disc 54 being quite close to valve seat 64 when primary solution is flowing but not so close as to impede normal maximum flow rates. Dimensions for a typical check valve in an administration set for parenteral solutions might be a screen with a porosity of about 25 microns and having a diameter of about 13 mm. and a thickness of about 0.0035 inch with a disc about 0.015 to about 0.030 inch thick, with the top of the disc spaced about 0.015 to about 0.021 inch from the valve seat.

Figure 7:
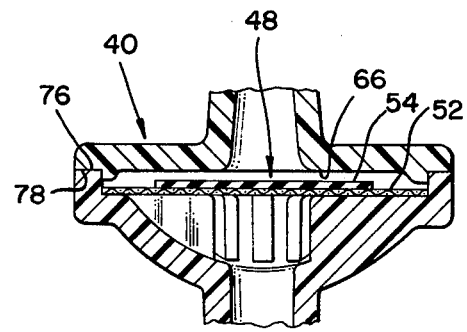
FIGS. 7 and 8 are fragmentary elevational views in cross-section of third and fourth embodiments, respectively, of the disc valve of this invention.
Figure 5:
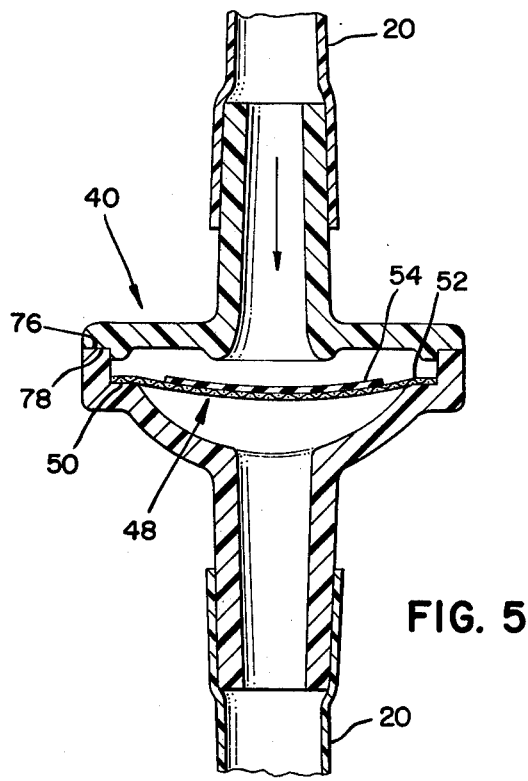
FIG. 5 is an elevational view in cross-section of a second embodiment of the disc valve of this invention.
Figure 8:
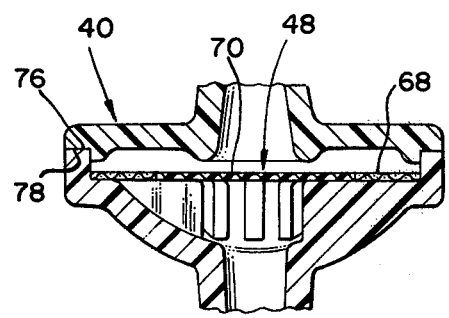
Figure 6:
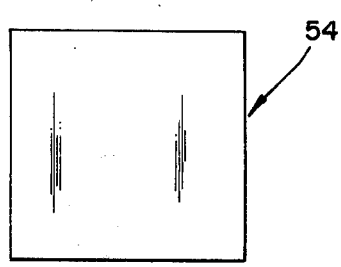
FIG. 6 is a plan view of a preferred embodiment of an imperforate means used in the disc valve.
Figure 9:
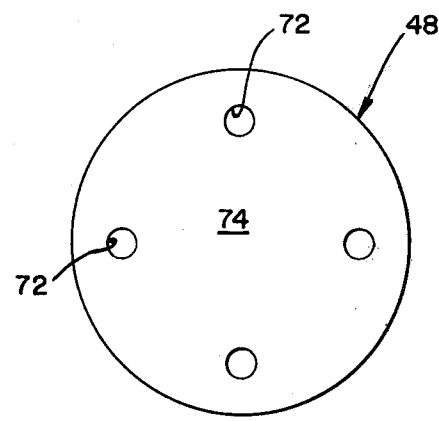
FIG. 9 is a plan view of still another version of a diaphragm in the valve of this invention.

Other modifications of the check valve are equally effective. For example, one need not have a screen support 56 as is shown in FIG. 5. Also, the valve seat need not be an annular projection such as that illustrated in FIGS. 2 and 3 but can be merely a flat portion 66 adjacent the passageway of inlet 42 as seen in the embodiment of FIG. 7. The flexible diaphragm 48 can be a unitary member such as that shown in the embodiment of FIG. 8 in which flexible screen 68 is impregnated with a polymeric substance in its central portion 70 to provide a smooth, impervious upper surface. The check valve may also have a flexible diaphragm 48 such as that in FIG. 9 in which a few large apertures 72 are positioned near the periphery of a flexible sheet 74 for fluids to flow through while maintaining an impervious central portion for seating against a valve seat.

In addition to its superior functioning as a valve member, the screen 52 (or 68) of the flexible diaphragm 48 also serves as a filter of particulate matter from a primary solution A.

The check valve of this invention, in addition to its use in the medical field, can be readily adapted for use in other areas, such as in the chemical industries. Here, much greater flow rates are usually required. In these situations, larger housings and screens are used. With screens or perforated sheets of greater cross-sectional area, the distance between the impervious disc or central portion and the valve seat can be greater to allow for larger flow rates and yet the flexible diaphragm 48 will still be responsive to slight pressure differentials.

Check valve CV is conveniently made by forming an inlet or upper part and an outlet or lower part. After sealing screen 52 (68) or sheet 74 at its periphery to shoulder 50 of the lower part and positioning disc 54 when necessary for those particular embodiments, the two parts are then sealed at edges 76 and 78.

Although several specific examples have been described to illustrate my invention, it is understood that certain changes to these examples can be made by those skilled in the art without departing from the spirit and scope of the invention.

I claim:

1. A check valve in a system for administering parenteral solutions comprising an elongated hollow housing having an enlarged portion between an inlet and an outlet, a thin flexible screen sealed peripherally within the enlarged portion and lying transversely to the inlet, means for supporting the screen, the support means being located in that part of the enlarged portion adjacent the outlet, a valve seat adjacent the passage at the inner end of the inlet, a thin resilient impervious disc separate from the screen and lying between the screen and the valve seat and adapted for releasably sealing the passage of the inlet, the screen and the disc being spaced from the valve seat with the screen being in an unflexed condition when the valve is in its normally open position whereby liquid flowing in the direction of the inlet to the outlet will pass freely around the disc and through at least a portion of the screen, whereas liquid when flowing in the direction of the outlet to the inlet effects movement of the screen against the disc sufficient to cause the disc to contact the valve seat and stop the flow of liquid when the pressure of the liquid at the outlet exceeds the pressure of the liquid at the inlet by at least about one inch of water.

2. The check valve of claim 1 wherein the support means comprises a plurality of ribs extending radially around the passage of the outlet.

3. The check valve of claim 2 wherein the foraminous member is a screen having a porosity of between 5 and 75 microns.

4. The check valve of claim 3 wherein the valve seat comprises a rounded annular projection surrounding the passage of the inlet.

5. The check valve of claim 4 wherein the resilient disc is substantially square.

6. A check valve in a system for administering parenteral solutions comprising a hollow housing having an enlarged portion between an inlet and an outlet, a thin flexible screen sealed peripherally within the enlarged portion and lying transversely to the inlet, the screen having a porosity in the range of about 5 to 75 microns, a plurality of ribs extending radially in that part of the enlarged portion adjacent the outlet for supporting the screen, a valve seat comprising a rounded annular projection surrounding the passage of the inlet, a thin resilient unattached disc positioned between the valve seat and the screen and having an area smaller than the area of the screen but sufficient to span the valve seat, the disc and the screen being spaced from the valve seat and with the screen being in an unflexed condition when the valve is in its normally open position, whereby liquid flowing in the direction of the inlet to the outlet passes freely around the disc and through the screen, whereas liquid flowing in the direction of the outlet to the inlet effects movement of the screen against the disc sufficient to cause the disc to contact the valve seat and stop the flow of liquid when the pressure of the liquid at the outlet exceeds the pressure of the liquid at the inlet by at least about one inch of water.

* * * * *